United States Patent [19]

Wolfinbarger, Jr.

[11] Patent Number: 5,976,104

[45] Date of Patent: *Nov. 2, 1999

[54] RECIRCULATION METHOD FOR CLEANING ESSENTIALLY INTACT BONE GRAFTS USING PRESSURE MEDIATED FLOW OF SOLUTIONS AND BONE GRAFTS PRODUCED THEREBY

[75] Inventor: Lloyd Wolfinbarger, Jr., Norfolk, Va.

[73] Assignee: LifeNet Research Foundation, Virginia Beach, Va.

[*] Notice: This patent is subject to a terminal disclaimer.

[21] Appl. No.: 08/646,520

[22] Filed: May 7, 1996

Related U.S. Application Data

[63] Continuation-in-part of application No. 08/395,113, Feb. 27, 1995, Pat. No. 5,556,379, which is a continuation-in-part of application No. 08/293,206, Aug. 19, 1994, abandoned.

[51] Int. Cl.$^6$ .................................................. A61M 31/00
[52] U.S. Cl. .............................. 604/49; 128/898; 422/33; 134/61
[58] Field of Search ................................ 128/898; 604/28, 604/48, 49; 600/36; 623/16; 435/1, 267, 268

[56] References Cited

U.S. PATENT DOCUMENTS

| | | | |
|---|---|---|---|
| 4,020,183 | 4/1977 | Asculai et al. ........................... | 424/341 |
| 4,169,123 | 9/1979 | Moore et al. .............................. | 422/29 |
| 4,207,689 | 6/1980 | Romera-Sierra et al. ................... | 35/20 |
| 4,258,722 | 3/1981 | Sessions et al. .......................... | 128/753 |
| 4,315,919 | 2/1982 | Shanbrom ................................ | 424/177 |
| 4,366,822 | 1/1983 | Altshuler ................................. | 128/752 |
| 4,412,985 | 11/1983 | Shanbrom ................................ | 424/78 |
| 4,456,589 | 6/1984 | Holman et al. ........................... | 424/95 |
| 4,526,751 | 7/1985 | Gartner .................................... | 422/37 |
| 4,553,974 | 11/1985 | Dewajnee ................................ | 8/94.11 |
| 4,637,931 | 1/1987 | Schmitz ................................... | 424/78 |
| 4,678,470 | 7/1987 | Nashef et al. ............................ | 623/16 |
| 4,695,536 | 9/1987 | Lindstrom et al. ........................ | 435/1 |
| 4,801,299 | 1/1989 | Brendel et al. ........................... | 623/1 |
| 4,891,221 | 1/1990 | Shanbrom ................................ | 424/101 |
| 4,923,677 | 5/1990 | Simon et al. ............................. | 422/37 |
| 4,946,792 | 8/1990 | O'Leary ................................... | 435/268 |
| 4,975,526 | 12/1990 | Kuberasampath et al. ............. | 530/350 |
| 4,994,030 | 2/1991 | Glowczewskie et al. ................ | 604/84 |
| 5,037,437 | 8/1991 | Matsen, III .............................. | 623/16 |

(List continued on next page.)

FOREIGN PATENT DOCUMENTS 952189 8/1982 U.S.S.R. .
964545 7/1964 United Kingdom .

OTHER PUBLICATIONS

"DMIN Asceptic Tissue Demineralization", a product brochure from Osteotech, Inc. 1993.

"Maximum Security for You and Your Patent", a product brochure regarding VIP Bone, from Cryolife, Inc., Feb. 12, 1992.

(List continued on next page.)

*Primary Examiner*—Wynn Wood Coggins
*Assistant Examiner*—Deborah Blyveis
*Attorney, Agent, or Firm*—Susanne M. Hopkins

[57] ABSTRACT

The present invention is directed to a process for cleaning large bone grafts using a pressure mediated flow of solutions, and to the bone grafts produced thereby where the bone grafts are suitable for transplantation into a human. The present method includes inducing a positive and/or negative pressure-mediated flow of solvent through an opening in the bone shaft of the large bone graft thereby removing bone marrow elements, as well as any bacteria particles and/or virus particles present. The bone grafts produced are suitable for transplantation into a human and are essentially free from viral and bacterial contamination, for example, free from HIV infectious particles.

31 Claims, 11 Drawing Sheets

U.S. PATENT DOCUMENTS

| | | | |
|---|---|---|---|
| 5,041,055 | 8/1991 | Roth | 452/140 |
| 5,047,030 | 9/1991 | Draenert | 606/65 |
| 5,106,626 | 4/1992 | Parsons et al. | 424/423 |
| 5,118,512 | 6/1992 | O'Leary et al. | 424/549 |
| 5,120,656 | 6/1992 | O'Leary et al. | 435/268 |
| 5,120,833 | 6/1992 | Kaplan | 530/354 |
| 5,133,756 | 7/1992 | Bauer et al. | 623/16 |
| 5,135,915 | 8/1992 | Czarniecki et al. | 514/21 |
| 5,167,961 | 12/1992 | Lussi et al. | 424/423 |
| 5,186,945 | 2/1993 | Shanbrom | 424/529 |
| 5,192,282 | 3/1993 | Draenert | 606/65 |
| 5,333,626 | 8/1994 | Morse et al. | 128/898 |
| 5,454,815 | 10/1995 | Geisser et al. | 606/85 |
| 5,513,662 | 5/1996 | Morse et al. | 128/898 |
| 5,591,398 | 1/1997 | Knaepler et al. | 422/38 |
| 5,628,782 | 5/1997 | Myers et al. | 923/1 |
| 5,634,879 | 6/1997 | Mueller-Glauser et al. | 600/36 |

OTHER PUBLICATIONS

"The Virucidal Capacity of a Surfactant/Iodophor–Based Viral Inactivation Process for Bone Allografts", a report of studies designed and funded by Cryolife, Inc., undated.

Sattar et al., "Survival and Disinfectant Inactivation of the Human Immunodeficiency Virus: A Critical Review", RID 1991; 13 (May–Jun.), pp. 430–447.

Exact. excerpts from "Product Specification, Discription, Patent Application & Supporting Documentation", by EXOxEMIS, Inc., Feb. 1991.

Klebanoff et al., "Virucidal Activity of H202–generating Bacteria; Requirement for Peroxidase and Halide", Dept. of Medicine, University of Washington School of Medicine, Seattle, Washington, Sep. 24, 1973.

Withrow et al., "Evaluation of the Antiretroviral Effect of Various Methods of Sterilization/Preserving Cortiocancellous Bone", presented at the 36th Annual Meeting, Orthopaedic Research Society, Feb. 5–8, 1990, New Orleans, Louisianna, Transactions of the Orthopaedic Research Society, 16, 1990, p. 226.

Garrison et al., "Comparison of Bacterial Contimation of Cadaveric Bone Allograft Collected Under Operating Room and Morgue Condition with and without the use of Decontaminating Process", presented at the Second Congress of the European Association of Tissue Bank, Athena, Greece, May 1993.

Morse, "A New Surfactant/Iodophor–Based Viral Inactivation Process (VIP) for Preparation of Bone Allografts", presented at the 16th Annual Meeting of the American Association of Tissue Banks, San Diego, Aug. 1992.

"Improve Performance of Your Immunoassay Systems and Immunodiagnostics Kits", a product brochure by Medicine & Applied Sciences, Inc., undated.

*Virginia Tissue Bank Procedure Manual*, Section 5.9.4.5, Copyright registered on Aug. 6, 1986.

Buck et al., "Human Immunodeficiency Virus Cultured From Bone. Implications for Transplantation", Clinical Orthopaedics and Related Research, No. 251, 1990.

*Navy Tissue Bank, Tissue Bank Coordinator Manual 10.* "Procurement of Deep Tissues and Bones", p. 9. (undated).

Shutkin, "Homologous–Serum Hepatitis following the Use of Refrigerated Bone–Bank Bone", The Journal of Bone and Joint Surgery, vol. 16–1, No. 1, 1954.

Hyatt et al., "Bone Grafting. The Procurement, Storage, and Clinical Use of Bone Homografts", The American Academy of Orthopaedic Surgeons, Ann Arbor, U.S.A., 1957.

"Transmission of HIV through Bone Transplantation: Case Report and Public Health Recommendations", Morbidity and Mortality Weekly Report, vol. 37, No. 39, 1988.

Kakaiya et al., "Tissue Transplant–Transmitted Infections", Transfusion, vol. 31, No. 3, 1991.

Tomford et al., "A Study of the Clinical Incidence of Infections in the Use of Banked Allograft Bone", The Journal of Bone and Joint Surgery, vol. 63–A, No. 2, 1981.

Furlini et al., "Antibody Response to Human Immunodeficiency Virus after Infected Bone Marrow Transplant", Eur. J. Clin, Microbiol. Infect. Dist., vol. 7, 1988.

Lord et al., "Infection in Bone Allografts. Incidence, Nature, and Treatment", The Journal of Bone and Joint Surgery, vol. 70–A, No. 3, 1988.

Bonfiglio et al., "The Immune Concept: Its Relation to Bone Transplantation", Annals New York Academy of Sciences, 1955.

Doppelt et al., "Operational and Financial Aspects of A Hospital Bone Bank", The Journal of Bone and Joint Surgery, vol. 63–A, No. 9, 1981.

Dirschi et al., "Topical Antibiotic Irrigation in the Prophylaxis of Operative Wound Infections in Orthopedic Surgery", Orthopedic Infection, vol. 22, No. 3, Jul. 1991.

Reynolds et al., "Clinical Evaluation of the Merthiolate Bone Bank and Homogenous Bone Grafts", The Journal of Bone and Joint Surgery, vol. 33–A, No. 4, 1951.

"MED CLEAN MARK II", a product brochure by Advanced International Marketing for a unit which includes a pressurized stream of water for bone debridement. (undated).

U.S. Department of Health and Human Services/Public Health Service," Transmission of HIV Through Bone Transplantation: Case Report and Public Health Recommendations," Morbidity and Morality Weekly Report, 37, 1988. pp. 597–599.

Mellonig, J. T. et al., "HIV Inactivation in a Bone Allograft", J. Periodontology, Dec. 1992, vol. 63, pp. 979–983.

RECIRCULATION METHOD FOR CLEANING ESSENTIALLY INTACT BONE GRAFTS USING PRESSURE MEDIATED FLOW OF SOLUTIONS AND BONE GRAFTS PRODUCED THEREBY

This application is continuation-in-part of application Ser. No. 08/395,113, filed Feb. 27, 1995, now U.S. Pat. No. 5,556,379 which is a continuation-in-part of application Ser. No. 08/293,206, filed Aug. 19, 1994 now abandoned, all of which are hereby incorporated by reference in their entirety herein.

FIELD OF THE INVENTION

This invention relates to a recirculation method for the cleaning of essentially intact bone grafts. The method possesses the attributes of being usable on a large number of bone grafts, including but not limited to the femur, tibia, ilia, and mandibular, prior to subsequent processing into specific grafts. The method involves the removal of bone marrow from the interstitial lumen and cancellous bone space by causing a flow of solvent through openings in the intact bone through the use of a pressure mediated flow of solvent. The solvent includes a combination of solutes which improve solvent penetration into and through the bone graft and increases the solubility of bone marrow, facilitating its removal from the essentially intact bone graft.

BACKGROUND OF THE INVENTION

Human bone obtained from cadaveric donors is typically procured under sterile conditions in an operating suite environment of local hospitals. The bone is stored frozen until it is further processed into small grafts under similar sterile conditions, or under clean-room conditions. Procurement and processing of human tissues is typically performed by groups certified by the American Association of Tissue Banks under standard operating procedures for the processing of each specific bone graft. Large bones such as the femur are thawed and debrided of excess tissue prior to being cut into smaller grafts. Processing of the smaller grafts includes cleaning of bone marrow from the cancellous bone spaces. This cleaning may use reduced or elevated temperatures, for example 4° C. to 65° C., and may also include the use of detergents, alcohol, organic solvents or similar solutes or combination of solutes designed to facilitate solubilization of the bone marrow.

SUMMARY OF THE INVENTION

It is the objective of the invention to provide a means of removing bone marrow from the luminal and cancellous bone spaces in essentially intact bone grafts.

In this regard, it is an object of the invention to provide intact bone graft material, essentially free of residual bone marrow, for use in the preparation of small bone grafts. Essentially intact bone grafts with minimal residual bone marrow offer additional advantages in that removal of bone marrow, which may harbor potential viral particles and/or viral genomes integrated into the genomes of specific cell types present in the bone marrow, reduces the potential for transmission of infective agents such as bacteria and viruses, especially the human immunodeficiency virus (HIV) in that cells capable of harboring this virus may be abundant in bone marrow of infected donors and their removal from essentially whole, bone grafts also reduces the potential initial quantity of viruses which may be present within the bone marrow cells removed.

Another object of this invention is to use alcoholic and soluble amphophil (detergent) solutions in the removal of bone marrow from bone grafts. Alcohols and detergents are viricidal towards enveloped viruses such as HIV and hepatitis and certain bacteria. Alcohol and detergent solutions also offer advantages of enhancing solubilization of bone marrow, reducing surface tension properties of aqueous solutions, and inactivating viruses and bacteria.

A further object of this invention is to provide methods for removing bone marrow from bone grafts after soft tissue removal and before their subsequently being cut into smaller bone grafts. The use of pressure induced flow of solvent through the bone grafts offers the advantage of causing a movement of solvent solubilized bone marrow in the opposite direction of the pressure source, of minimizing structural damage to the cancellous bone by using minimally invasive cleaning methods, and of permitting containment of the effluent bone marrow/solvent in containers which may be safely handled and disposed of without exposure of the processing personnel. Use of hypotonic solutions induces bone marrow cell swelling and fragmentation and solubilization of cells. The movement of solvent in the opposite direction of the pressure source will result in the continual exchange of solvent with the result that solubilized bone marrow is removed and bone marrow which has not been solubilized will be exposed to additional fresh solvent. Thus the continual replacement of solvent will reduce the need for greater concentrations of solubilization enhancing components. A further object of the present invention is to provide a method for cleaning essentially intact bone grafts where the solvent recirculates through the bone graft.

Detergents are amphophil compounds which facilitate solubilization of relatively insoluble lipids present in, for example, bone marrow, yet at higher concentrations tend to form micellar structures (Helenius, A. and Simons, K. Solubilization of Membranes by Detergents, *Biochim. Biophys. Acta* 415:29–79 (1975). The formation of micellar structures tend to limit the effective concentration range for detergent solutions and thus soaking of bone in a given volume of detergent solution may not be totally effective in that the absolute amount of detergent present is limited. If the amount of lipid material to be solubilized exceeds the solubilization capability of the detergent present, lipid solubilization will not be complete. By continually changing the detergent solution over time, all solubilizable lipid present in a bone graft is completely solubilized. Restricted flow of solvent through the cartilaginous ends and normal structural openings of the bone minimizes mechanical and/or structural damage to the cancellous bone by causing a slow flow rate of solvent through the trabecular bone space occupied by bone marrow.

A yet further object of the invention is to provide mechanical devices which permit attachment of solvent lines to the various large bone grafts being cleaned by the process of pressure induced solvent flow, which permit attachment of the solvent containers around the bone grafts being cleaned, and to permit the collection and containment of effluent materials from the bone grafts. These mechanical devices can be sterilized by a variety of procedures, for example, by autoclaving, and the devices form tight seals with the bone grafts being cleaned.

The containment of aspirated bone marrow/solvent is made possible by use of disposable containers for collection of the aspirate. In addition, it becomes possible to add strong viral/bacterial inactivators, for example sodium hypochlorite, to the fluids in the disposable collection containers after removal of the cleaned bone to further inactivate potential pathogenic and/or biohazardous biomaterials. Filters between the pressure source and the collection containers further prevents the potential spread of biohazardous materials. The use of more traditional soaking procedures, such as described in U.S. Pat. No. 5,333,626 (Preparation of Bone for Transplantation, Morse & Shanbrom) to remove bone marrow involves the use of pressurized flow of solution as a rapidly moving stream, for example Pulsavac Lavage, which dislodges bone marrow by impact of the solvent on the exposed cut surfaces of small bone grafts. Such procedures tend to generate aerosols of tissue and solvent which can be hazardous to processing personnel. The present invention eliminates this hazard. The present invention is directed to a method for cleaning an essentially intact bone graft using a pressure redirected flow of solvent while simultaneously (sonicating) the essentially intact bone graft with the solvent in a container of ultrasonic cleaning device. The present invention is also directed to bone grafts essentially free from bacterial, fungal and viral contamination. The present invention is further directed to bone grafts produced using the present methods.

BRIEF DESCRIPTION OF THE DRAWINGS

FIG. 1 illustrates the cleaning of bone using a positive pressure mediated flow of solvent through an essentially intact bone.

FIG. 2 illustrates the cleaning of transected bone using positive pressure mediated flow of solvent.

FIGS. 3A and 3B illustrate a flow diagram of the present recirculation method for cleaning an essentially intact bone grafts using a positive pressure mediated flow of solvent.

FIG. 4 illustrates changes in absorbance at 410mm with volume of detergent drawn through a typical bone graft. Concentrations of proteins (microgram/ml of eluent) eluting from porcine proximal femurs being flushed with deionized/distilled water ⊕, 0.01X Allowash™ in Dulbecco's Phosphate Buffered Saline (DPBS) (▲), and 0.01X solution in a 30% (vol:vol) ethanolic solution in deionized/distilled water (X). Flushing procedure utilizes peristaltic pump induced flow of solutions and eluent materials are collected as 15 ml volumes using a fraction collector. Aliquots of eluent are assayed for protein concentrations using a protein assay. The data included in this figure is used only to illustrate the relative quantities of bone marrow solubilized by the different solutions shown and is not intended to document bone marrow solubilization as described in the patent application.

FIG. 5 illustrates the present method using a negative pressure mediated flow of solvent to clean bone.

FIG. 6 illustrates the present method usisng a negative pressure mediated flow of solvent to clean transected bone by drawing solvent to waste.

FIG. 7 illustrates the present method using a negative pressure mediated flow of solvent to clean transected bone where a negative pressure mediated flow to recirculate the solvent through the bone.

FIGS. 8A and 8B illustrate a flow diagram for cleaning essentially intact bone grafts using a negative pressure mediated flow of solvent.

FIG. 9 illustrates the flushing of a femur head.

DETAILED DESCRIPTION OF THE PREFERRED EMBODIMENTS

I. Definitions

Figure 1:
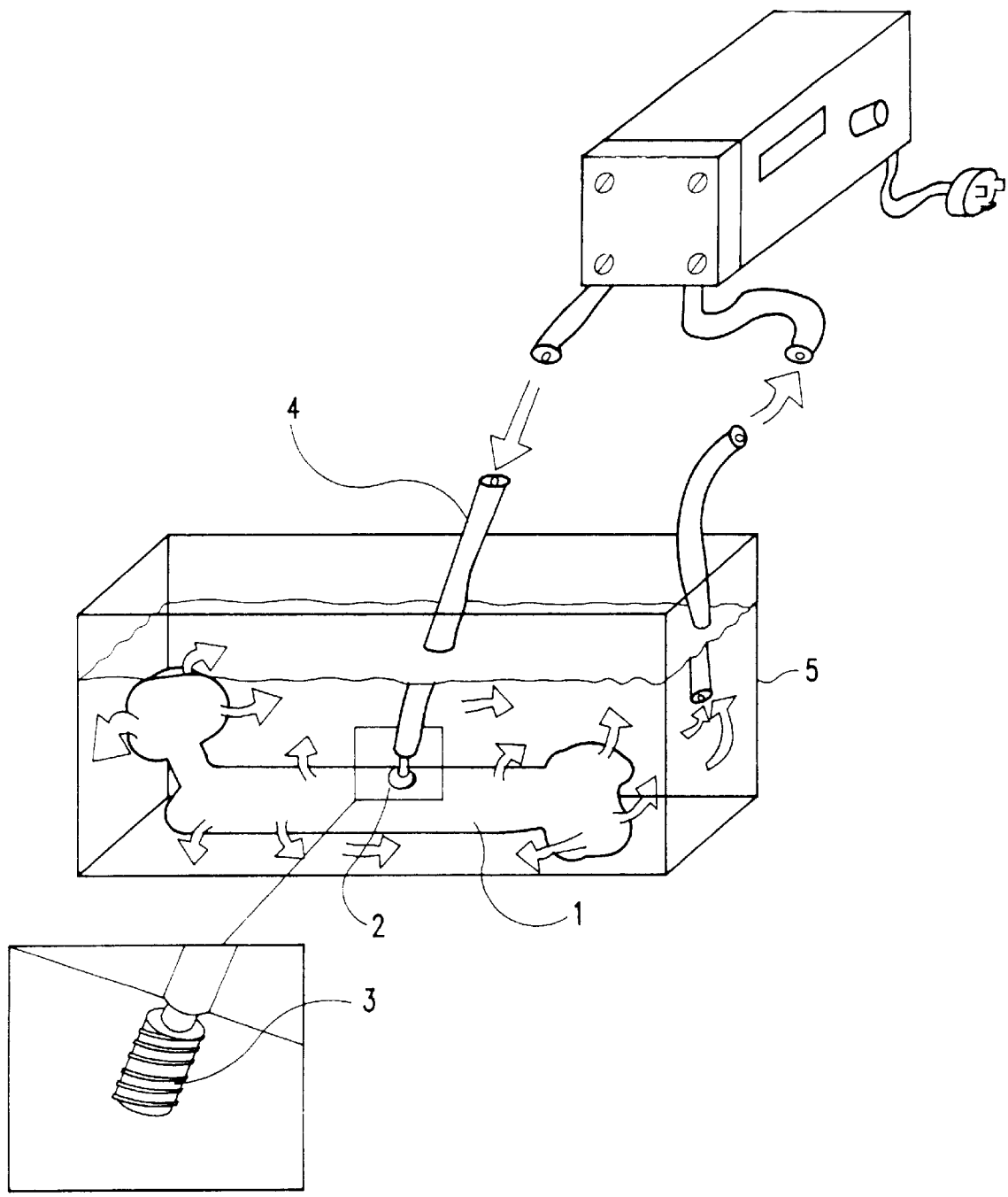
FIG. 1.

The below definitions serve to provide a clear and consistent understanding of the specification and claims, including the scope to be given such terms.

Allowash™ Solution. By the term "Allowash™ solution" is intended those (compositians) disclosed in co-pending U.S. patent application Ser. No. 08/620,856 incorporated herein by reference. Examples of suitable Allowash™ compositions include: a cleaning composition containing essentially about 0.06 wt % polyoxgethylene-4-lauryl ether; about 0.02 wt % poly(ethylene glycol)-p-nonyl-phenyl-ether; about 0.02 wt % octylphenol-ethyleneoxide and endotoxin free deionzied/distilled water.

Pressure Mediated Flow of Solvent. By the term "pressure mediated flow of solvent" is intended for the purposes of the present invention, a flow of solvent induced by positive or negative pressure.

Cleaning Container. By the term "cleaning container" is intended for the purpose of the present invention any rigid or deformable container of a size sufficient to contain the bone graft being processed. This sterile cleansing container may be the "beaker" of a Branson ultrasonic cleaner, for example, Models 1210, 2210, and 3210, as size of the bone graft dictates, capable of operating at between 20 and 50 Khz at temperatures up to 69±5° C.

Detergent. By the term "detergent" is intended any agent which through a surface action that depends on it possessing both hydrophilic and hydrophobic properties and/or exerts oil-dissolving (cleansing) and/or antibacterial and/or antiviral effects, and can include but is not limited to: anionic detergents, cationic detergents acridine derivatives, and long-chain aliphatic bases or acids.

Ultrasonic Cleaner. By the term "ultrasonic cleaner" is intended any ultrasonic cleaning device capable of operating at: from 20 KHz to 50 KHz, preferably from about 40 KHz to about 47 KHz, and includes, for example, Branson ultrasonic cleaner model nos.: 1210, 2210, 3210, 5210 and 8210; or any similar ultrasonic cleaner.

Bone Marrow. By the term "bone marrow" is intended for the purposes of the present invention the highly cellular hematopoietic connective tissue filling the medullary cavities and spongy epiphyses of bones which may harbor bacterial and/or viral particles and/or fungal particles.

Decontaminating Agent. By the term "decontaminating agent" is intended one or more agents which remove or inactivate/destroy any biohazardous material potentially present in the bone marrow of a bone graft, for example, such materials including but not limited to: bacteria, virus, and/or fungi; with such decontaminating agents including, for example, but not limited to one or more of the following: an antibacterial agent; an antiviral agent; an antimycotic agent; an alcohol for example, methyl, ethyl, propyl, isopropyl, butyl, and/or t-butol; sodium hydroxide; hydrogen peroxide; and/or any detergent.

Negative Pressure. By the term "negative pressure" is intended for the purposes of this invention a pressure below atmospheric pressure, i.e., less than one atmosphere.

Positive Pressure. By the term "positive pressure" is intended for the purposes of this invention a pressure at or above one atmosphere, i.e., greater than or equal to one atmosphere.

Essentially Closed System. By the term "essentially closed system" is intended for the purposes of the present invention, a system which prevents the potential spread of any potentially biohazardous materials present in bone marrow, i.e. bacterial and/or viral and/or fungal particles; for example, a system whereby aspirated bone marrow and solvent is contained and thus does not come into contact with processing personal and whereby aerosols of tissues are not generated.

Essentially Free From. By the term "essentially free from" is intended a bone graft where the material removed (i.e., bone marrow, viral, fungal, and/or bacterial particles) from the bone graft is not detectable using detection means known in the art at the time of filing of this application.

Essentially Intact Bone Graft. By the term "essentially intact bone graft" is intended for the purposes of the present invention any whole bone including, for example, the femur, tibia, ilia, humorous, radius, ulna, ribs, whole vertebrae, mandibular, and/or any bone which can be retrieved from a donor with minimal cutting of that bone, for example, one half of an ulna, a femur cut in half to yield a proximal half and a distal half, and/or at least a substantial portion of a whole bone, i.e., at least one-quarter of a whole bone.

Solvent. By the term "solvent" is intended for the purposes of the present invention, a liquid cleaning composition capable of: facilitating the solubilization of lipid, facilitating bone marrow removal, inactivating viral and/or bacterial particles, and/or disrupting cell membranes, which may contain, but is not limited to, one or more of the following: sterile water; saline; a detergent; an alcohol, for example, ethanol and/or isopropanol, solvents, a combination of solutes desired to facilitate solubilization of bone marrow including for example, one or more of: Allowash™ solution disclosed in co-pending patent application Ser. No. 08/620,856 herein incorporated by reference; a chelating agent; a virucidal agent; bacteriocidal agent; antimycotic agent; sodium hydroxide; or similiar strong base; organic and/or inorganic acids; and hydrogen peroxide.

Figure 2:
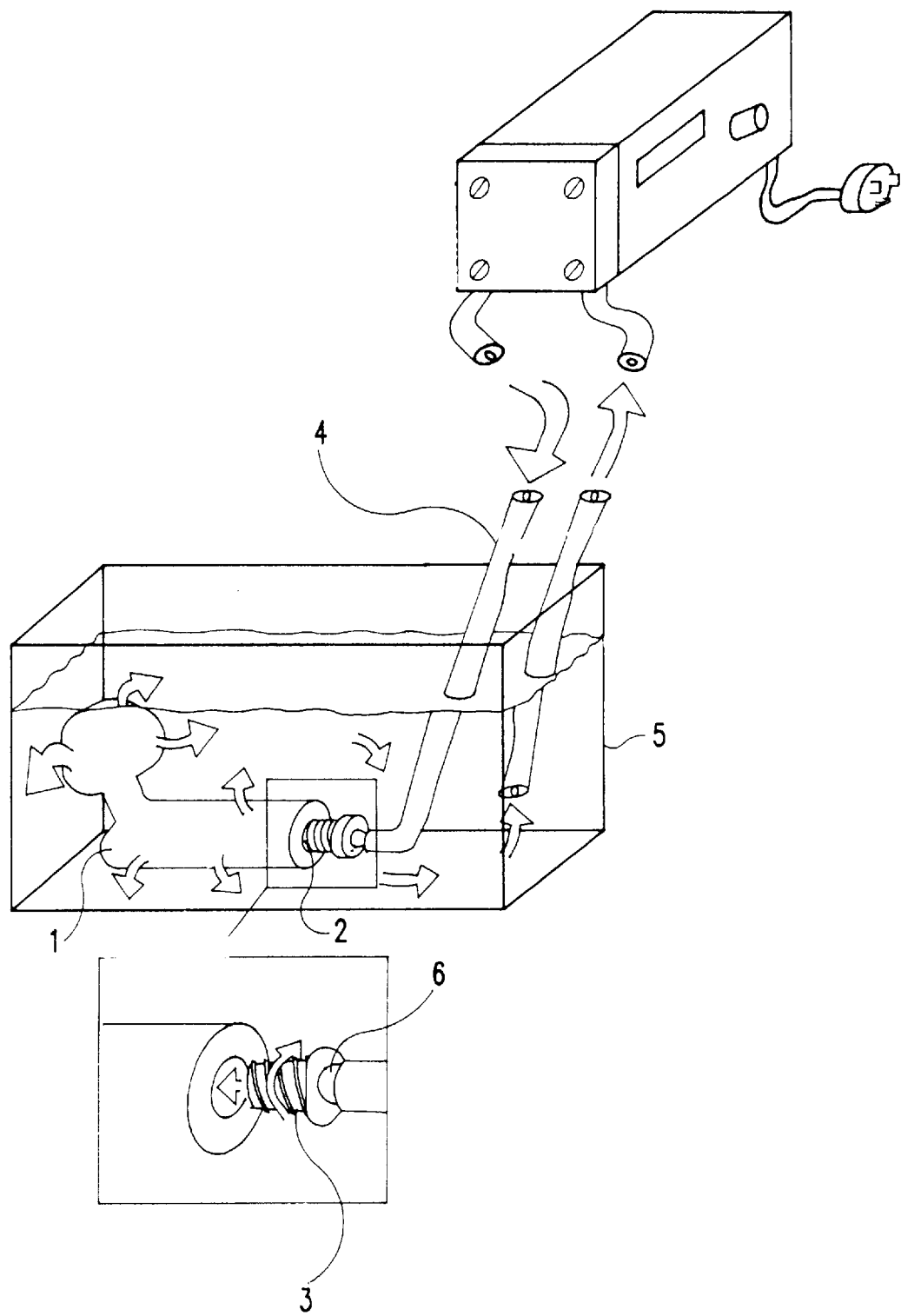
FIG. 2.

II Recirculation Method A: Using Positive and Negative Pressure to Move Solvent(s) Through Bone Graft The formulation of a preferred embodiment of the present invention is highly reproducible and results in a bone graft essentially free from bone marrow elements, bacterial and/or viral particles. In this regard, the process for cleaning essentially intact bone grafts involves the thawing of bone materials procured from cadaveric donors. Following thawing under sterile conditions at room temperature, the bone is prepared for attachment of the solvent line by drilling a small hole approximately midway between the proximal and distal ends or by transecting the whole bone approximately midway between the proximal and distal ends. The bone is attached to the solvent source and placed into the solvent solution in a sterile cleaning container. This sterile cleaning container may be the "beaker" of a Branson ultrasonic cleaner, for example, Models 1210, 2210, 3210, as size of the bone graft dictates, capable of operating at between 20 and 50 Khz at temperatures up to 69±5° C. As solvent solution is forced through the bone graft, it is collected in a disposable container or recirculated. Portions of the preferred embodiments of the present invention are illustrated in FIGS. 1 and 2.

The pressure source used to push the solvent solution through the bone graft will be sufficient to generate a flow of solution from a pressurized system, preferably a peristaltic pumping system (for example a Q2V piston size with a V200 Controller from FMI) approximating up to 2304 milliliters per minute. The use of peristaltic pumping systems facilitates retention of sterility in the solutions being induced to flow through the bone grafts. The actual pressure level or pumping rate is adjusted such that the flow rate of solution through the bone graft does not occur so rapidly that the bone marrow is not effectively solubilized, but rapidly enough to effectively remove solubilized bone marrow. Flow rates of solvent should range from 180 and 2,304 mls per minute with the preferred rates being in the range from 500 to 2,000 mls per minute, most preferably from 1,000 to 1,500 mls per minute. A representative flow diagram illustrating, but not limited to, a series of steps to be taken in cleaning a bone using the recirculation method using a positive pressure mediated flow of solvent is shown in FIG. 3.

Figure 3A:
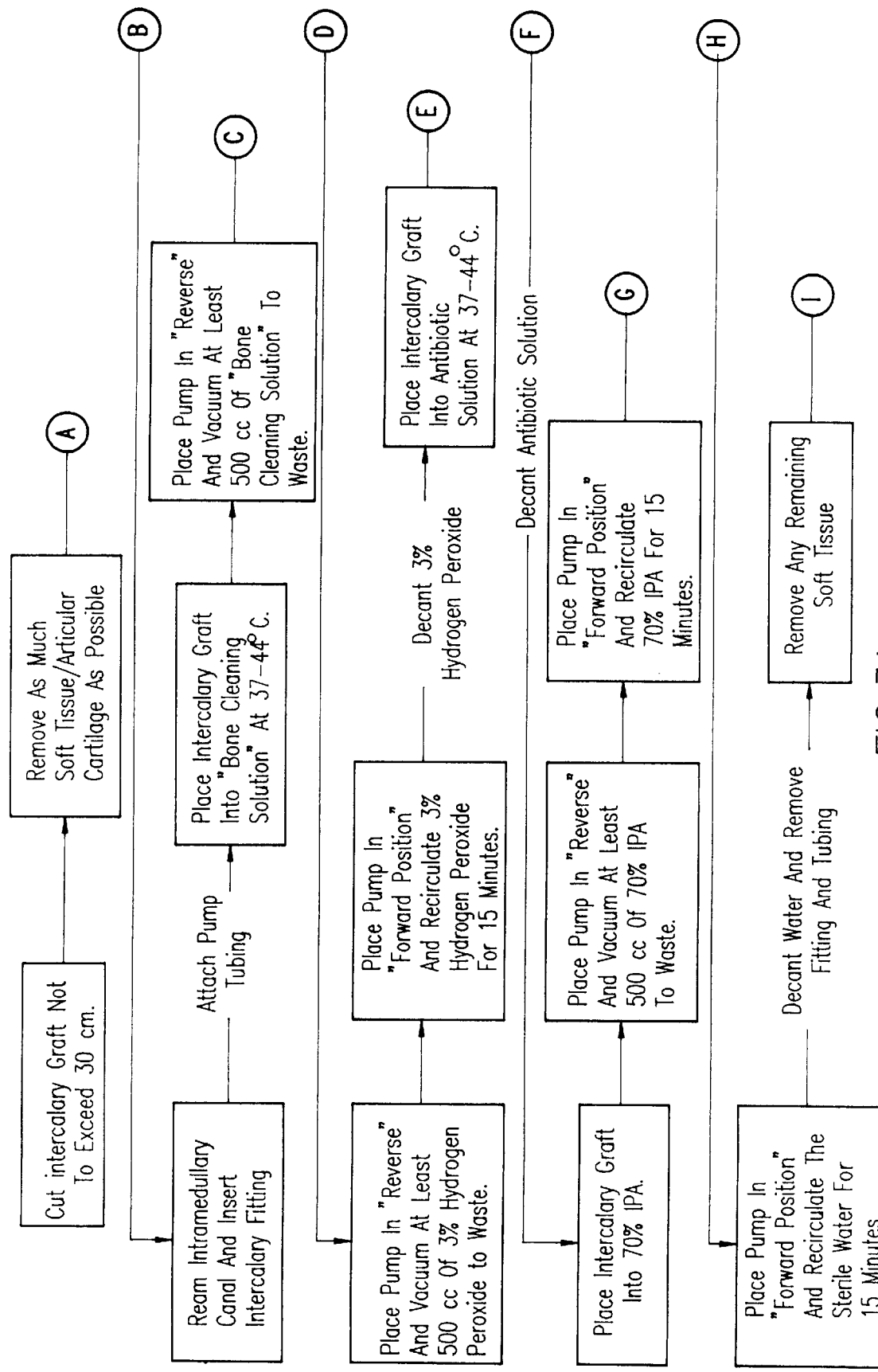
FIGS. 3A and 3B.
Figure 3B:
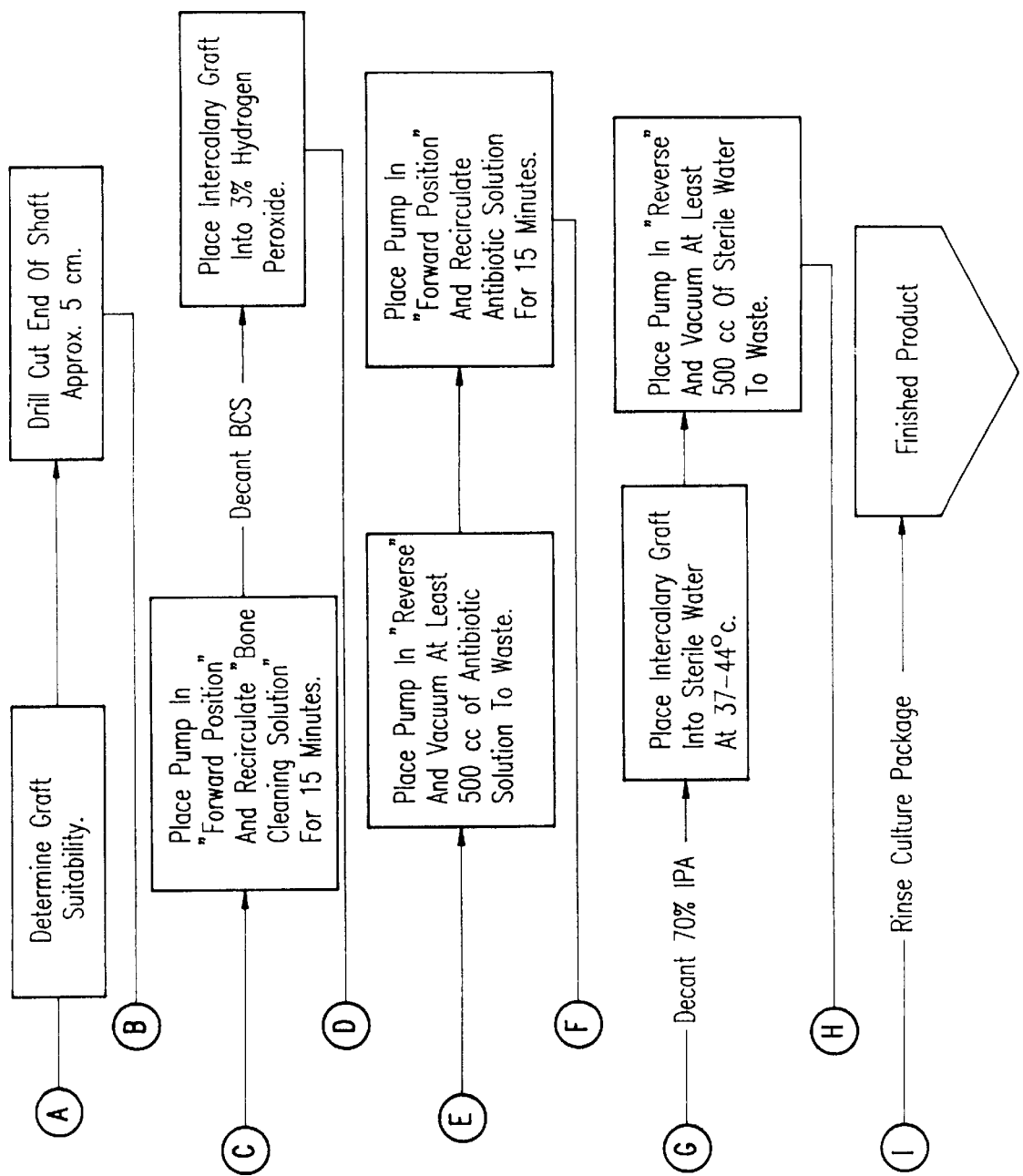
Figure 4:
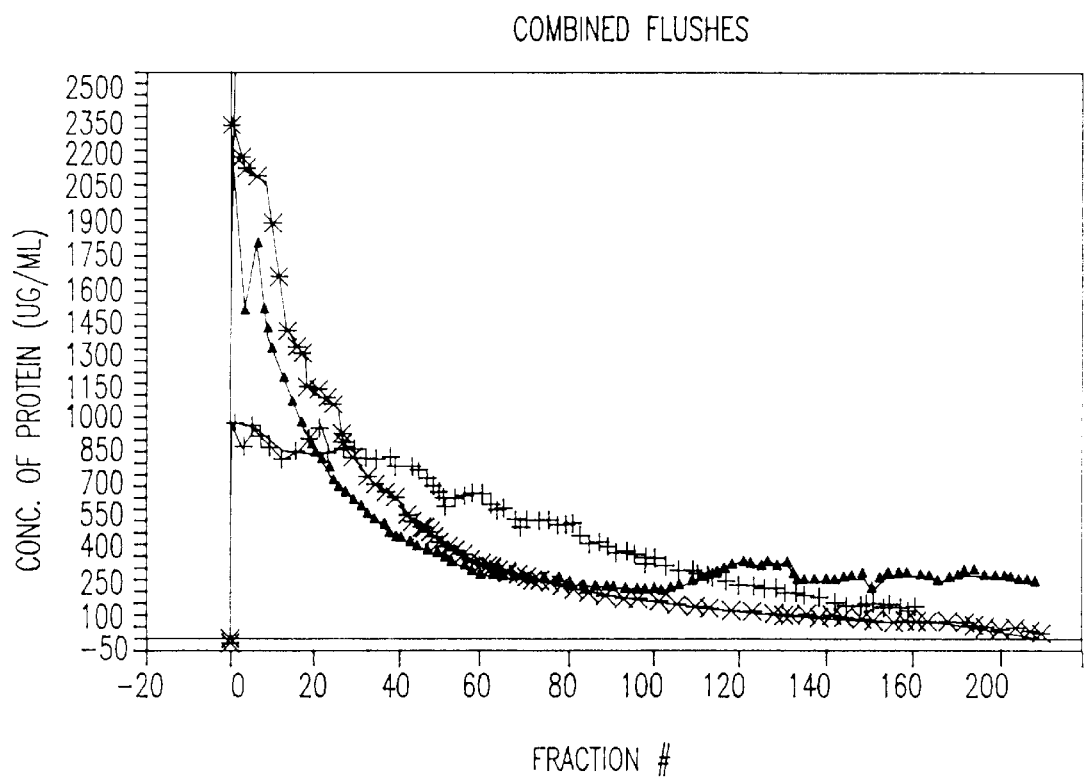
FIG. 4.

The first solvent Bone Cleaning Solution or BCS as described in FIG. 3 to be drawn using a negative pressure flow or flushed using a positive pressure flow, through the bone graft can consist of, for example, a sterile mixture of detergent and/or ethanol or other alcohol, in endotoxin-free deionized/distilled water. Detergents utilized include, but are not restricted to, ionic and/or nonionic detergents such as polyoxyethylene alcohols (Brij series, Lubrol W, etc.), polyethylene glycol p-isooctylphenylethers (Triton X series), Nonidet P-40, nonoxynol 9, polyoxyethylene nonylphenol (Triton N series, Surfonic N series, Igepal CO series), polyoxyethylene sorbitol esters (Tween series, Emasol series), the formulation known as Allowash™ Solution (LifeNet Research Foundation, Virginia Beach, Va., pending patent application Ser. No. 08/620,856) in concentrations ranging between 0.001 weight percent to 2.0 weight percent with the preferred concentrations being in the range of 0.005 to 1.0 weight percent, most preferably from 0.01 to 0.5 weight percent. The concentration of alcohol which may be used in the first solution ranges from 5 to 95% (volume to volume) with the preferred range being from 10 to 30% (volume to volume). Suitable alcohols include but are not limited to: ethanol, isopropanol, butanol, n-propanol and methanol.

The second solvent to be drawn using a negative pressure flow or flushed using a positive pressure flow through the bone graft can include, for example, hydrogen peroxide in endotoxin-free deionized/distilled water (for example, from 1 to 5%, preferably 3% hydrogen peroxide), alcoholic solutions of water, or isotonic saline in endotoxin-free deionized/distilled water. The second solvent may be added to the container following removal of the first solution by simply pouring the second solvent into the container. During changes of the solution in the container, the solvent flow should be shut off in order to facilitate solvent changing in the container. The purpose of the second solvent is to reduce the amount of the first solvent in the bone graft and/or to deliver additional agents to be used in processing of the essentially intact bone graft. For example, addition of hydrogen peroxide (3%), ethanol, or isopropyl alcohol (50% to 100%, vol to vol) to a washing solution serves to further reduce bacterial, fungal, and/or viral contaminants which might be present in the bone graft. The use of absolute (100%) ethanol or isopropyl alcohol or other alcohol further serves to dehydrate the bone, thereby reducing subsequent time needed for freeze-drying. Since the flow of solvent through the bone graft is less restricted during the flushing with the second, third, or subsequent solvent(s), the level of pressure used should be appropriately reduced to maintain an appropriate flow rate of 1,000 to 1,500 mls per minute. The volumes of the second, third, or subsequent, solvents may vary depending on the concentration of detergent and/or alcohol used in the first solvent, but in general should approximate a volume 10 to 100-fold greater than the volume of the bone graft being processed.

Following completion of flushing of bone graft with the cleaning solvents, and washing solvents as illustrated in FIG. 3, the bone graft may be removed from the sterile container and processed into smaller bone grafts via procedures previously established for the production of such grafts or additional solvents may be flushed through the bone graft to add additional processing procedures/solutions into the total bone cleaning process.

Optional components may also be added to either the first, second, third, or subsequent solvents being used to clean and flush, respectively, the bone graft, including, but not limited to, antibiotics, antiviral agents (for example peroxide generating agents such as Exact™ a trademarked product marketed by ExOxEmis, Inc., San Antonio, Tex.), hydrogen peroxide, permeation enhancers (for example fatty acid esters such as laurate, myristate and stearate monoesters of polyethylene glycol), organic acids (for example citric acid) or dilute solutions of strong acids (for example hydrochloric acid).

III. Recirculation Method A: In summary

1. Initially about 200 to 1,000 mls, preferably about 400 to 600 mls and most preferably about 500 mls of a first solvent containing one or more detergents is drawn through the bone graft to waste using a negative pressure mediated flow of solvent at a temperature of from 37° C. to 44° C.

2. Thereafter the bone is flushed using a positive pressure mediated flow with a second solvent optionally containing a detergent (this second solvent may be the same or different from the first), where the second solvent is flushed to waste or recirculated through the bone. This flushing or recirculation is carried out for about 5 to 25 minutes, preferably about 10 to 20 minutes, and most preferably about 15 minutes, or until bone marrow removal is complete as indicated by absorbance of the effluent material at 410 nm. (Steps 1 and 2 may optionally be repeated using the same or a different solvent, if necessary, to facilitate further cleaning. The necessity for further cleaning, as well as the selection of the particular solvent, can be readily determined by one of ordinary skill in the art without undue experimentation, for example, by monitoring absorbance of the effluent material at 410 nm).

3. The second solvent is then removed from the bone graft by either: (a) flushing to waste using a positive pressure mediated flow with a third solvent, or (b)(i) drawing according to step 1 (about 500 mls) of a third solvent to waste using a negative pressure flow followed by (ii) flushing using a positive pressure flow, a third solvent through the bone; where the third solvent preferably contains a decontaminating agent.

4. A fresh volume of the third solvent is then optionally recirculated using a positive pressure flow through the bone for a time period from about 5 to 25 minutes, preferably from about 10 to 20 minutes, and most preferably about 15 minutes.

5. Steps 3–4 are optionally repeated using new volumes of the same or different solvents. Preferably, steps 3 and 4 are repeated using a solvent containing one or more antibiotics and/or antivirals and/or antimycotics followed by removal of the antibiotics/antivirals/antimycotics, steps 3 and 4 may optionally be repeated using a solvent containing one or more alcohols, and finally repeated to remove the solvent containing alcohols, using sterile water as the solvent in steps 3 and 4.

The order of use of solvents and the particular composition of a particular solvent used in the present process is not critical as long as the first solvent used is a solvent containing one or more detergents. The present process includes at least performing steps 1 and 2 using a first solvent containing one or more detergents.

Figure 6:
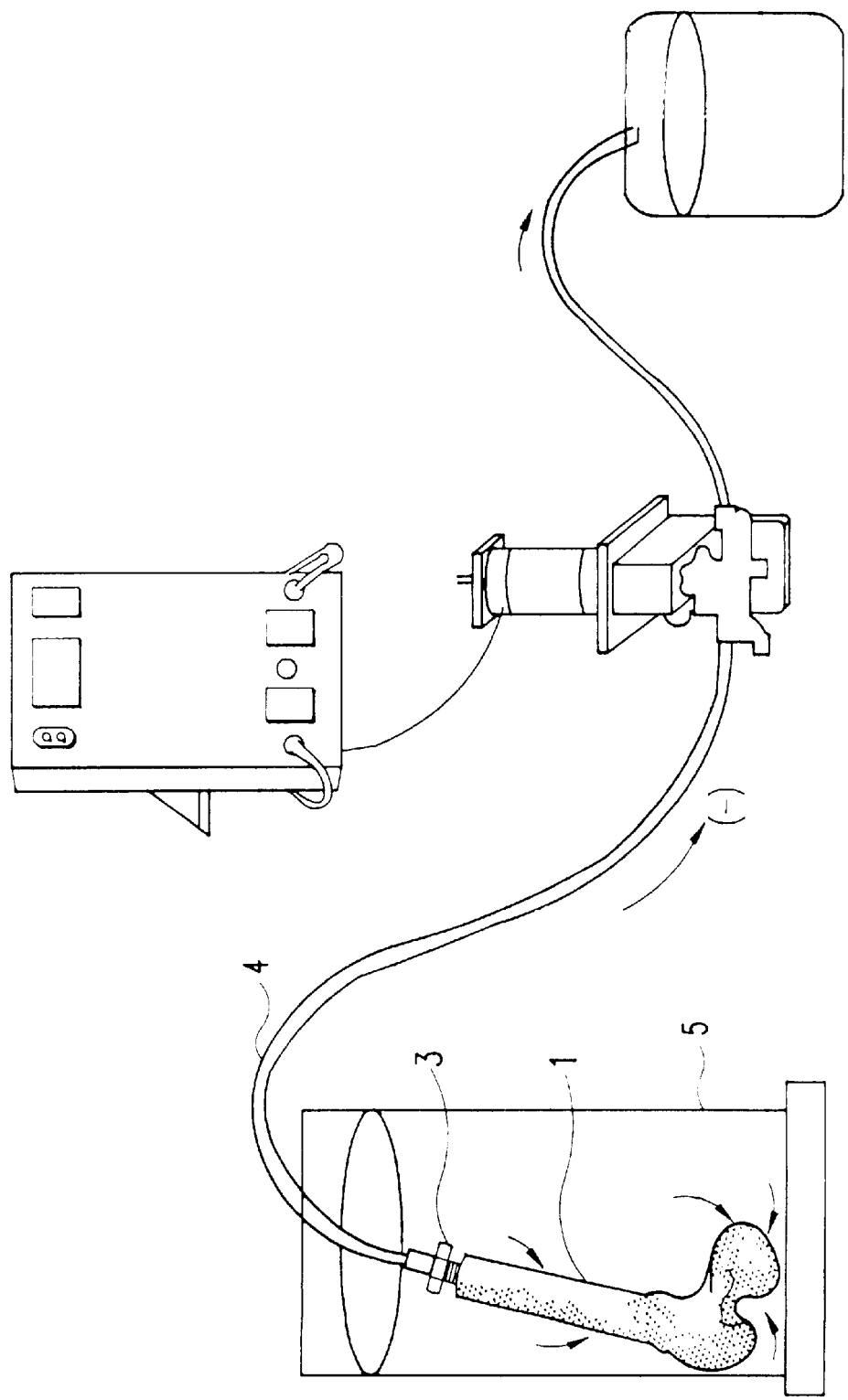
FIG. 6.
Figure 7:
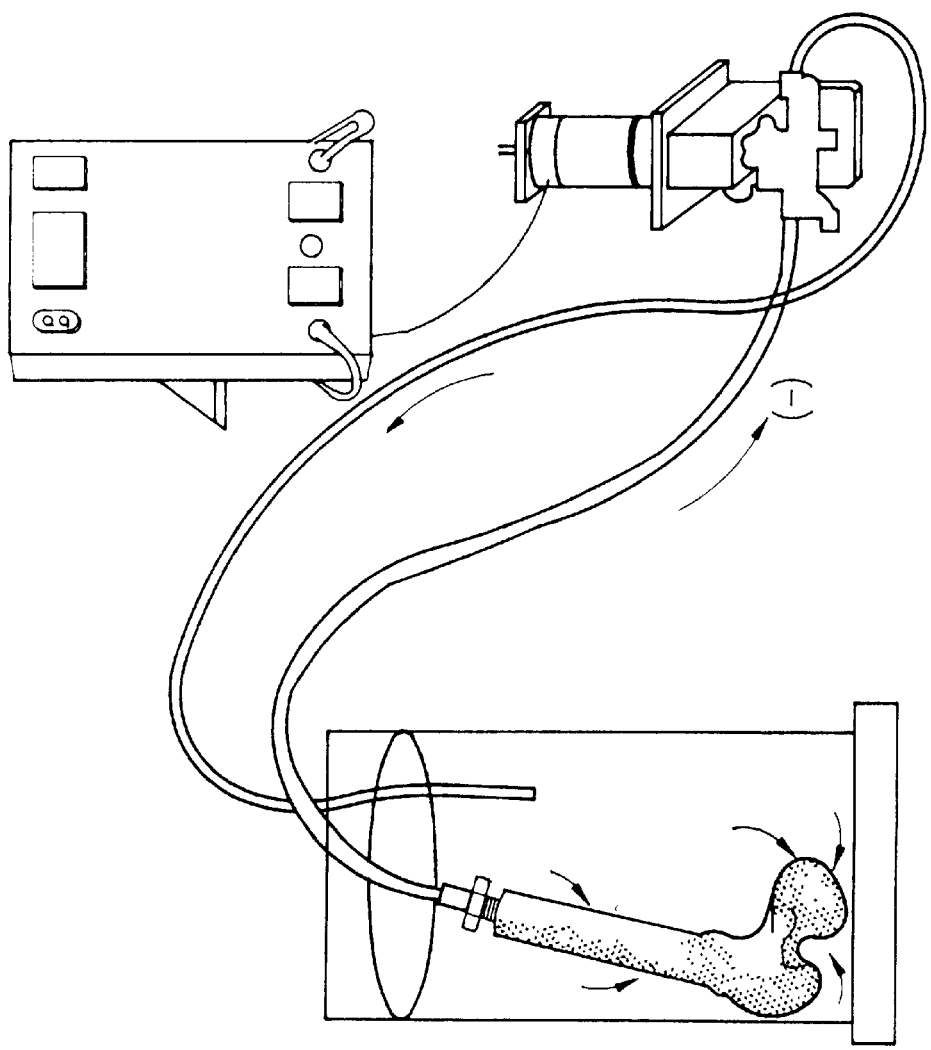
FIG. 7.
Figure 8A:
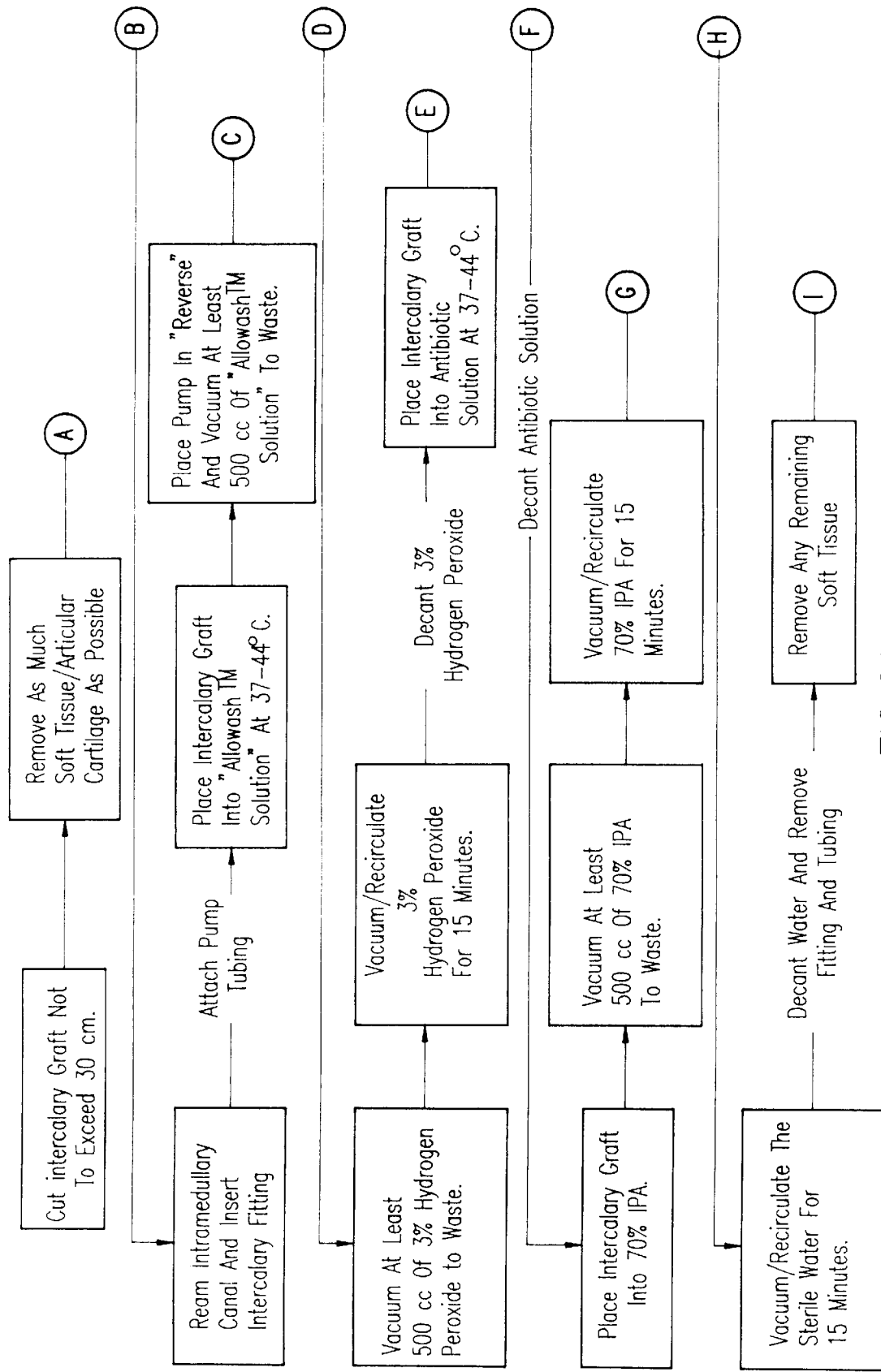
FIGS. 8A and 8B.
Figure 8B:
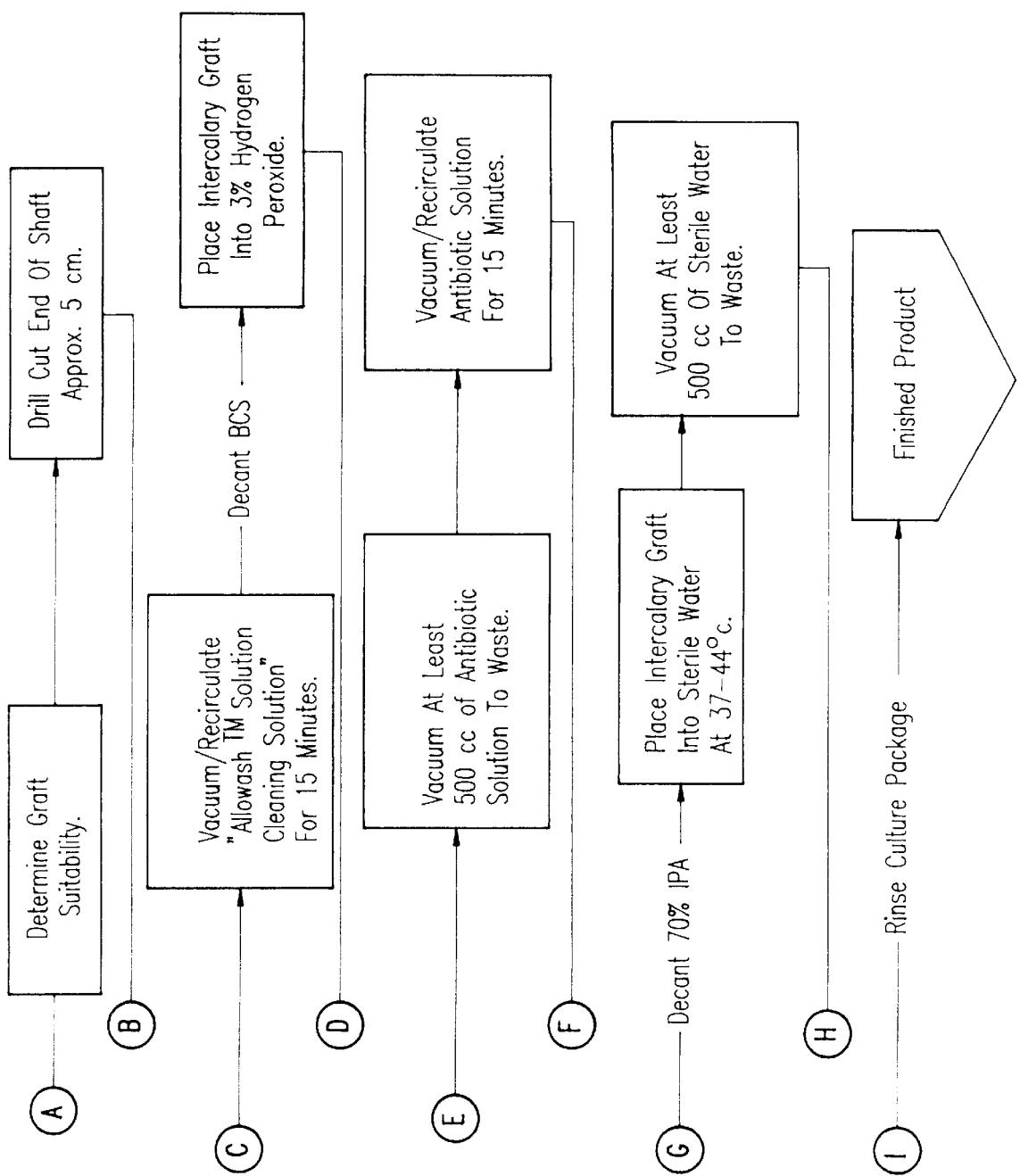

IV. Recirculation Method B: Using Negative Pressure to Pull Solvent Through a Bone Graft The formulation of a preferred embodiment of the present invention is highly reproducible and results in the production of a graft which is essentially free from bone marrow elements, bacterial particles, viral particles and/or fungal particles. In this regard, the process for cleaning essentially intact bone grafts involves the thawing of bone materials procured from cadaveric donors. Following thawing under sterile conditions at room temperature, the bone is prepared for attachment of the solvent line by drilling a small hole (preferably approximately midway between the proximal and distal ends of the bone) or by transecting the whole bone (preferably approximately midway between the proximal and distal ends of the bone). The bone is attached to the solvent source and placed into the solvent solution in a sterile cleaning container. This sterile cleaning container may be the "beaker" of a Branson ultrasonic cleaner, for example, Models 1210, 2210, 3120, as size of the bone graft dictates, capable of operating at between 20 and 50 Khz at temperatures up to 69±5° C. As solvent solution is pulled through the bone graft, it is collected in a disposable container or recirculated. Portions of the preferred embodiments of the present invention are illustrated in FIGS. 6, 7 and 8.

The pressure source used to pull solution through the bone grafts will be sufficient to generate a flow of solution from a system under negative pressure, preferably a peristaltic pumping system (for example a Q2V piston size with a V200 Controller from FMI) approximating up to 2304 milliliters per minute. The use of peristaltic pumping systems facilitates retention of sterility in the solutions being induced under negative pressure to flow through the bone graft. The actual pressure level or pumping rate is adjusted such that the flow rate of solution through the bone graft does not occur so rapidly that the bone marrow is not effectively solubilized, but rapidly enough to effectively remove solubilized bone marrow. Flow rates of solvent should range from 180 and 2,304 mls per minute with the preferred rates being in the range from 500 to 2,000 mls per minute, most preferably from 1,000 to 1,500 mls per minute. A representative flow diagram illustrating, but not limited to, a series of steps to be taken in cleaning a bone using the recirculation method using a negative pressure mediated flow of solvent is shown in FIG. 8.

The first solvent (Bone Cleaning Solution or BCS as described in FIG. 3) to be pulled through the bone graft can consist of, for example, a sterile mixture of detergent and/or ethanol or other alcohol in endotoxin-free deionized/distilled water. Detergents utilized include, but are not restricted to, ionic and/or nonionic detergents such as polyoxyethylene alcohols (Brij series, Lubrol W, etc.), polyethylene glycol p-isooctylphenylethers (Triton X series), Nonidet P-40, nonoxynol 9, polyoxyethylene nonylphenol (Triton N series, Surfonic N series, Igepal CO series), polyoxyethylene sorbitol esters (Tween series, Emasol series), the formulation known as Allowash™ Solution (LifeNet Research Foundation, Virginia Beach, Va., pending patent application Ser. No. 08/620,856) in concentrations ranging between 0.001 weight percent to 2.0 weight percent with the preferred concentrations being in the range of 0.005 to 1.0 weight percent, most preferably from 0.01 to 0.5 weight percent. The concentration of alcohol which may be used in the first solution ranges from 5 to 95 % (volume to volume) with the preferred range being from 10 to 30% (volume to volume). Suitable alcohols include but are not limited to: methanol, ethanol, propanol, isopropanol, n-propanol, and/or butanol.

The second solvent to be drawn through the essentially intact bone graft can include, for example, hydrogen peroxide in endotoxin-free deionized/distilled water (for example, from 1 to 5%, preferably 3% hydrogen peroxide), alcoholic solutions of water, or isotonic saline in endotoxin-free deionized/distilled water. The second solution may be added to the container following removal of the first solution by simply pouring the second solution into the container. During changes of the solution in the container, the solvent flow should be shut off in order to facilitate solvent changing in the container. The purpose of the second solution is to reduce the amount of the first solution in the bone graft and/or to deliver additional agents to be used in processing of the whole bone graft. For example, addition of hydrogen peroxide (3%), ethanol, or isopropyl alcohol (50% to 100%, vol to vol) to a washing solution would serve to further reduce bacterial, fungal, and/or viral contaminants which might be present in the bone graft. The use of absolute (100%) ethanol or isopropyl or other alcohol further serves to dehydrate the bone, thereby reducing subsequent time needed for freeze-drying. Since the negative pressure induced flow of solution through the bone graft is less restricted during the use of the second, third, or subsequent solvent(s), the level of pressure used should be appropriately adjusted to maintain an appropriate flow rate of 1,000 to 1,500 mls per minute. The volumes of the second, third, or subsequent solvent(s) may vary depending on the concentration of detergent and/or ethanol or other alcohol used in the first solution, but in general should approximate a volume 10 to 100-fold greater than the volume of the bone graft being processed.

Following completion of negative pressure mediated drawing of the bone graft with the cleaning and washing solvents as illustrated in FIG. 6, the bone graft may be removed from the sterile container and processed into smaller bone grafts via procedures previously established for the production of such grafts or additional solutions may be flushed through the bone graft to add additional processing procedures/solvents into the total bone cleaning process.

Optional components may also be added to either the first, second, third, or subsequent solvents being used including, but not limited to, antimycotics, antibiotics, antiviral agents (for example peroxide generating agents such as Exact™ a trademarked product marketed by ExOxEmis, Inc., San Antonio, Tex.), hydrogen peroxide, permeation enhancers (for example fatty acid esters such as laurate, myristate and stearate monoesters of polyethylene glycol), organic acids (for example citric acid) or dilute solutions of strong acids (for example, hydrochloric acid).

V. Recirculation Method B: In Summary

1. Initially about 200 to 1,000 mls, preferably about 400 to 600 mls and most preferably about 500 mls of a first solvent containing one or more detergents is drawn through the bone graft to waste using a negative pressure mediated flow of solvent at 37° C. to 44° C.

2. Thereafter a second solvent which may be the same or different from the first is then: (a) drawn to waste or (b) recirculated through the bone using a negative pressure medicated flow of solvent. This drawing or recirculation is carried out for about 5 to 25 minutes, preferably about 10 to 20 minutes, and most preferably about 15 minutes, or until bone marrow removal is complete as indicated by absorbance of the effluent material at 410 nm. (Steps 1 and 2 may optionally be repeated using the same or a different solvent, if necessary, to facilitate further cleaning. The necessity for further cleaning, as well as the selection of the particular solvent, can be readily determined by one of ordinary skill in the art without undue experimentation, for example, by monitoring absorbance of the effluent material at 410 nm).

3. The second solvent is then removed from the bone graft by drawing a third solvent according to step 1 (about 500 mls) to waste using a negative pressure flow. The third solvent preferably contains a decontaminating agent.

4. A fresh volume of the third solvent is then optionally drawn or recirculated through the bone for a time period of from about 5 to 25 minutes, preferably from about 10 to 20 minutes, and most preferably about 15 minutes using a negative pressure redirected flow of solvent.

5. Steps 3–4 are optionally repeated using new volumes of the same or different solvents. Preferably, steps 3 and 4 are repeated using a solvent containing one or more antibiotics and/or antivirals and/or antimycotics followed by removal of the antibiotics/antivirals/antimycotics, steps 3 and 4 may optionally be repeated using a solvent containing one or more alcohols, and finally repeated to remove the solvent containing alcohols, using sterile water as the solvent in steps 3 and 4.

The order of use of solvents and the particular composition of a particular solvent used in the present process is not critical as long as the first solvent used is a solvent containing one or more detergents. The present process includes at least performing steps 1 and 2 using a first solvent containing one or more detergents.

The following examples illustrate processing of large bone grafts according to the present invention.

A. Cleaning a Bone Graft Using Recirculation Method A (use of negative and positive pressure to draw solution(s) through a bone graft) (See FIG. 3)

EXAMPLE I

A femur (1) (See FIG. 5) is thawed and a hole 2 approximately ¼ to ⅝ inch outside diameter is drilled in the bone shaft approximately midway between the distal and proximal ends of the bone. The hole need only be drilled deep enough to penetrate the cortical bone such that the tapping port (3) may be securely inserted into the hole. The pressure line (4) is attached securely to the tapping port. Two to three liters of a solution of 10% isopropanol vol:vol and Allowash™ Solution at a concentration of 0.01X are added to a sterile container (5) designed to hold approximately 3 liters and the bone graft with attached solvent line is placed into the container, immersing it towards the bottom of the container. The container in this case is the beaker of an ultrasonic cleaner. The temperature of the cleaning solution is adjusted to 37° C. to 45° C. prior to addition of the bone graft and the container with bone graft is placed into a heated water bath, also at 37° C. to 45° C. Power is applied to the ultrasonic cleaning "beaker," in this case a Branson model 2210 47 Khz, with a 2.8 liter tank ("beaker") capacity and negative pressure, equivalent to 25 to 30 inches of Hg, is applied.

Figure 5:
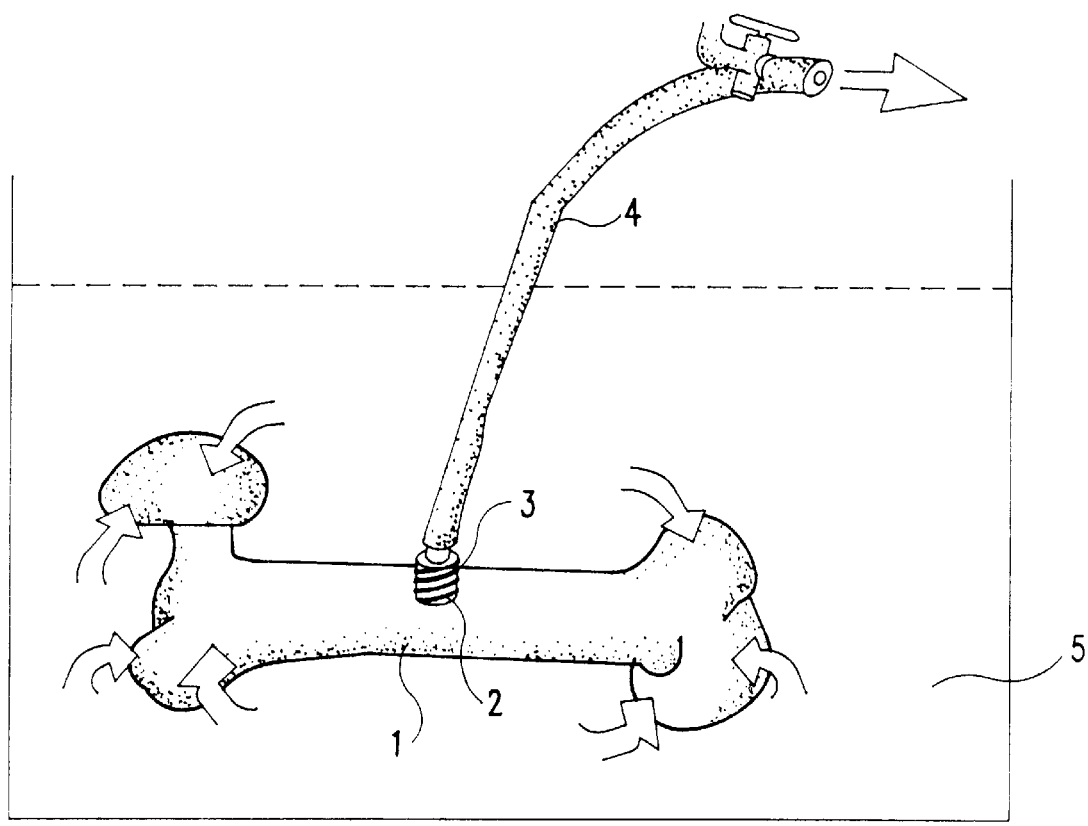
FIG. 5.

Vacuum is applied to the system through the use of a closed peristaltic pumping system to achieve a reverse solvent flow through the bone (1) with solution being directed to waste (FIG. 5). Approximately 500 ml of Bone Cleaning Solution is normally sufficient to effect a removal of the majority of bone marrow residue. Thereafter, the flow is directed into the bone using positive pressure (FIG. 1) such that the flow rate of solution through the bone graft is maintained at approximately 1200 ml per minute by adjusting the pumping rate of the peristaltic pump. The solution flowing into the container is red(ish) initially, turning to a color similar to that of serum as bone marrow is removed from the graft. By sampling the effluent material being removed from the bone graft, it is possible to monitor completion of bone marrow removal. Specifically, by measuring absorbance at 410 nm it is possible to determine when essentially all of the bone marrow is removed from the bone graft.

After flushing using a positive pressure mediated flow for approximately 15 minutes or until bone marrow removal is complete as indicated by absorbance at 410 nm, the flow to the system is discontinued and the container is emptied and refilled with 1 to 4 liters of 3% hydrogen peroxide in endotoxin-free deionized/distilled water and a positive pressure mediated solvent flow is reapplied to the system. The hydrogen peroxide solution is flushed through the bone graft at approximately 1200 mls per minute to remove the detergent solution and to effect further cleaning of the bone graft. Following the flushing of detergent solution from the bone graft, solvent flow is discontinued to the system and the hydrogen peroxide solution is emptied and an antibiotic solution is added to the container. A negative pressure flow is applied to the bone such that approximately 500 ml of antibiotic solution is pumped to waste. The flow of antibiotic solution is then directed using positive pressure into the bone graft and allowed to circulate for approximately 15 minutes. Solvent flow is discontinued and the antibiotic solution is decanted and 70% isopropanol is added to the container. Approximately 500 mls of isopropanol is drawn through the bone graft using a negative pressure flow and pumped to waste. Solvent flow is then directed into the bone graft using positive pressure and recirculated (as illustrated in FIG. 1) for approximately 15 minutes. The isopropanol is decanted after solvent flow is stopped and the container is refilled with sterile deionized endotoxin-free water. Approximately 500 mls of water is drawn through the bone graft using a negative pressure flow and directed to waste. The flow of water is then directed into the bone graft using positive pressure and recirculated for approximately 15 minutes. Finally, the water is decanted, the bone graft is removed from the container and the solvent line and tapping port are removed. Any remaining soft tissue may be removed at this time and the bone graft is now ready for further processing as required (i.e., into small cut bone grafts).

EXAMPLE II

A femur (1) is thawed and cut in half using a bone saw (FIG. 6). The proximal end of the femur (1) is used in this example, however, the distal end of the femur would be similarly processed. Pulsavac lavage with sterile water is used to remove bone marrow from the luminal space and the solvent line (4) attachment port (3) is screwed into the luminal cavity of the cut bone. Two to four liters of a solution of 10% isopropanol vol:vol and Allowash™ Solution in sterile ondotoxin-free deionized/distilled water at a concentration of 0.01X are added to a sterile container (5) designed to hold approximately 4 liters and the bone graft with attached solvent line (4) is placed into the container, immersing it towards the bottom of the container. The temperature of the cleaning solution is adjusted to 37° C. to 45° C. prior to addition of the bone graft and the container with bone graft is placed into a heated water bath, also at 37° C. to 45° C.

Vacuum is applied to the system through the use of a closed peristaltic pumping system to achieve a negative pressure solvent flow through the bone with solution being directed to waste. Approximately 500 ml of Bone Cleaning Solution is normally sufficient to effect the removal of the majority of bone marrow residue. At this point, the flow is directed into the bone using positive pressure (FIG. 2) such that the flow rate of solution through the bone graft is maintained at approximately 1200 ml per minute by adjusting the pumping rate of the peristaltic pump. The solution flowing into the container is red(ish) initially, turning to a color similar to that of serum as bone marrow is removed from the graft. By sampling the effluent material being removed from the bone graft, it is possible to monitor completion of bone marrow removal. Specifically, by measuring absorbance at 410 nm it is possible to determine when essentially all of the bone marrow is removed from the bone graft.

After flushing for approximately 15 minutes or until completion of bone marrow removal as indicated by absorbance at 410 nm, the flow to the system is discontinued and the container is emptied and refilled with 1 to 4 liters of 3% hydrogen peroxide in endotoxin-free deionized/distilled water and a negative pressure mediated solvent flow is reapplied to the system. The hydrogen peroxide solution is initially directed to flow into the bone using negative flow with approximately 500 mls of solutions directed to waste. The flow of solution is then directed into the bone graft using positive pressure mediated flow such that the solution is flushed through the bone graft at approximately 1200 mls per minute to remove the detergent solution and to effect further cleaning of the bone graft. Following the flushing of detergent solution from the bone graft, solvent flow is discontinued to the system and the hydrogen peroxide solution is emptied and an antibiotic solution is added to the container.

A negative flow is applied to the bone such that approximately 500 ml of antibiotic solution is pumped to waste. The flow of antibiotic solution is then directed using positive pressure into the bone graft and allowed to recirculate for approximately 15 minutes. Solvent flow is discontinued and the antibiotic solution is decanted and 70% isopropanol is added to the container. Approximately 500 mls of isopropanol is drawn through the bone graft using a negative pressure flow and pumped to waste. Solvent flow is then directed into the bone graft using positive pressure and recirculated for approximately 15 minutes. The isopropanol is decanted after solvent flow is stopped and the container is refilled with sterile deionized endotoxin-free water. Approximately 500 mls of water is drawn through the bone graft using a negative pressure flow and directed to waste. The flow of water is then directed into the bone graft using positive pressure and recirculated for approximately 15 minutes. Finally, the water is decanted, the bone graft is removed from the container and the solvent line and tapping port removed. Any remaining soft tissue may be removed at this time and the bone graft is now ready for further processing as required.

EXAMPLE III

Referring to FIG. 1, a femur (1) is thawed, and a hole (2) approximately ¼ to ⅝ inch outside diameter is drilled in the bone shaft approximately midway between the distal and proximal ends of the bone. The hole need only be drilled deep enough to penetrate the cortical bone such that the tapping port (3) may be securely inserted into the hole. The solvent line (4) is attached securely to the tapping port. Two liters of a solution of 10% ethanol and Allowash™ Solution at a concentration of 0.01X are added to a container designed to hold approximately 3 liters and the bone graft with attached solvent line is placed into the container, immersing it towards the bottom of the container. The temperature of the cleaning solution was adjusted to 45° C. prior to addition of the bone graft and the container with bone graft is placed onto a warming plate, also at 45° C. Positive pressure solvent flow, 1,000 to 1,500 mls/minute, is applied to the system. The flow rate of solution through the bone graft is maintained at approximately 1,200 mls per minute by adjusting the pump rate of the peristaltic pump.

The solution collected in the disposable container is initially dark red(ish), turning to a color similar to that of serum as bone marrow is removed from the graft. By sampling the effluent material being removed from the bone graft it is possible to monitor completion of bone marrow removal by measuring absorbance at 410 nm and it is thus possible to determine when essentially all of the bone marrow is removed from the bone graft. After flushing approximately 3 liters of solution through the bone graft over 15 minutes, the solvent flow to the system is discontinued and the container is refilled with 1 to 3 liters of 3% hydrogen peroxide (vol:vol) in endotoxin-free deionized/distilled water and solvent flow is reapplied to the system. The hydrogen peroxide deionized/distilled water solution is flushed through the bone graft at approximately 1100 mls per minute for 15 minutes to remove the detergent solution. Following the flushing of detergent solution from the bone graft, solvent flow is discontinued to the system and the bone graft is removed from the container and the solvent line and tapping port removed. The bone graft is now ready for further processing into small bone grafts as required.

EXAMPLE IV

For cleaning smaller portions of an essentially intact bone graft (FIG. 9) for example, femur heads (1), it is not necessary to use the plastic containers, or the pressure induced flow of flushing and/or washing solvents. Instead, a large volume syringe (3) with an approximate 18 gauge needle (3) may be used to cause a flow of solvent through the cancellous bone space in the smaller portions of whole bone grafts. In the cleaning process illustrated in FIG. 9, a femur head is cut from the proximal end of a femur. A small hole (2) is drilled in the approximate center of the cut cross-sectional area to a depth approximating the beginning of the cortical bone distally to the point at which the hole is initiated. The diameter of the hole should be slightly smaller than the outside diameter of the needle which is to be inserted. Once the needle is inserted, flow of cleaning solvent may be caused to occur by means of pressure applied on the syringe plunger in the syringe attached to the needle inserted into the cancellous bone space of the small bone graft, for example, the a femur head. The cleaning solvents utilized are equivalent to those described in previous examples given. Cleaning solvents may be removed from the cancellous bone space by attaching a fresh syringe to the needle and flushing endotoxin-free ultra-pure water through the cancellous bone space. The volumes of cleaning solvents necessary to clean a typical femur head, as illustrated, may range from 200 mls to 500 mls with the preferred volume being 250 to 300 mls. The volumes of washing solvents necessary to remove residual cleaning solution from a typical femur head, as illustrated, may range from 50 mls to 200 mls, with the preferred volume being 100 to 150 mls.

B. Cleaning Bone Grafts Using Recirculation Method B (use of only negative pressure to pull solution(s) through a bone graft) (See FIG. 8)

EXAMPLE V

A femur (1) is thawed and a hole (2) approximately ¼ to ⅝ inch outside diameter is drilled in the bone shaft approximately midway between the distal and proximal ends of the bone. The hole need only be drilled deep enough to penetrate the cortical bone such that the tapping port (3) (FIG. 5) may be securely inserted into the hole. The pressure line (4) is attached securely to the tapping port. Two to three liters of a solution of 10% isopropanol vol:vol and Allowash™ Solution in sterile endotoxin-free deionized/distilled water at a concentration of 0.01X are added to a sterile container designed to hold approximately 3 liters and the bone graft with attached solvent line is placed into the container, immersing it towards the bottom of the container. The temperature of the cleaning solution was adjusted to 37° C. to 45° C. prior to addition of the bone graft and the container with bone graft is placed into a heated water bath, also to 37° C. to 45° C. The sterile cleaning container may be the "beaker" of a Branson ultrasonic cleaner, for example, Models 1210, 2210, 3120, as size of the bone graft dictates, capable of operating at between 20 and 50 Khz at temperatures up to 69±5° C. Power is applied to the ultrasonic cleaning "beaker," in this case a Branson model 2210 47 Khz, with a 2.8 liter tank ("beaker") capacity and negative pressure, equivalent to 25 to 30 inches of Hg, is applied.

Vacuum is applied to the system through the use of a closed peristaltic pumping system to achieve a negative pressure solvent flow through the bone with solution being directed to waste. Approximately 500 ml of Bone Cleaning Solution is normally sufficient to effect a removal of the majority of bone marrow residue. At this point, the negative pressure flow is adjusted such that the flow rate of solution through the bone graft is maintained at approximately 1200 ml per minute by adjusting the pumping rate of the peristaltic pump. The solution flowing into the container is red(ish) initially, turning to a color similar to that of serum as bone marrow is removed from the graft. By sampling the effluent material being removed from the bone graft, it is possible to monitor completion of bone marrow removal by measuring absorbance at 410 nm it is possible to determine when essentially all of the bone marrow is removed from the bone graft.

After flushing using negative pressure for approximately 15 minutes, the flow to the system is discontinued and the container is emptied and refilled with 1 to 4 liters of 3% hydrogen peroxide in endotoxin-free deionized/distilled water and a negative pressure mediated solvent flow is reapplied to the system. The hydrogen peroxide solution is drawn through the bone graft at approximately 1200 mls per minute to remove the detergent solution and to effect further cleaning of the bone graft. Following the removal of detergent solution from the bone graft, solvent flow is discontinued to the system and the hydrogen peroxide solution is emptied and an antibiotic solution is added to the container. A negative flow is applied to the bone such that approximately 500 ml of antibiotic solution is pumped to waste. The negative pressure flow of antibiotic solution is allowed to circulate for approximately 15 minutes. Solvent flow is discontinued and the antibiotic solution is decanted and 70% isopropanol is added to the container. Approximately 500 mls of isopropanol is drawn through the bone graft using a negative pressure flow and pumped to waste. The negative pressure solvent flow is then continued and solvent is recirculated for approximately 15 minutes. The isopropanol is decanted after solvent flow is stopped and the container is refilled with sterile deionized endotoxin-free water. Approximately 500 mls of water is drawn through the bone graft and directed to waste. The negative pressure flow of water is then recirculated for approximately 15 minutes. Finally, the water is decanted, the bone graft is removed from the container and the solvent line and tapping port are removed. Any remaining soft tissue may be removed at this time and the bone graft is now ready for further processing as required (i.e., into small bone grafts).

EXAMPLE VI

A femur is thawed (FIG. 6), soft tissue/articular cartilage is removed, and the femur cut in half using a bone saw. The proximal end of the femur (1) is used in this example, however, the distal end of the femur would be similarly processed. The solvent line (4) attachment port (3) is screwed into the luminal cavity of the cut bone (1). Two to four liters of a solution of 10% isopropanol vol:vol and Allowash™ Solution in sterile endotoxin free deionized/ distilled water at a concentration of 0.01X are added to a sterile container (5) designed to hold approximately 4 liters and the bone graft with attached solvent line is placed into the container, immersing it towards the bottom of the container. The temperature of the cleaning solution was adjusted to 37° C. to 45° C. prior to addition of the bone graft and the container with bone graft is placed into a heated water bath, also at 37° C. to 45° C.

Vacuum is applied to the system through the use of a closed peristaltic pumping system to achieve a negative pressure solvent flow through the bone with solution being directed to waste. Approximately 500 ml of Bone Cleaning Solution is normally sufficient to effect the removal of the majority of bone marrow residue. The solution flowing into the container is red(ish) initially, turning to a color similar to that of serum as bone marrow is removed from the graft. By sampling the effluent material being removed from the bone graft, it is possible to monitor completion of bone marrow removal by measuring absorbance at 410 nm it is possible to determine when essentially all of the bone marrow is removed from the bone graft.

At this point, the negative pressure flow is adjusted such that the flow rate of solution through the bone graft is maintained at approximately 1200 ml per minute by adjusting the pumping rate of the peristaltic pump. The solution is allowed to recirculate (FIG. 7).

After recirculation for approximately 15 minutes, the flow to the system is discontinued and the container is emptied and refilled with 1 to 4 liters of 3% hydrogen peroxide in endotoxin-free deionized/distilled water and a negative pressure mediated solvent flow is reapplied to the system. The hydrogen peroxide solution is drawn through the bone with approximately 500 mls of solutions directed to waste. The negative pressure flow of solution is then adjusted such that the solution is drawn through the bone graft at approximately 1200 mls per minute to remove the detergent solution and to effect further cleaning of the bone graft. The solution is allowed to recirculate through the bone for about 15 minutes. Following the removal of detergent solution from the bone graft, solvent flow is discontinued to the system and the hydrogen peroxide solution is emptied and an antibiotic solution is added to the container.

A negative pressure flow is applied to the bone such that approximately 500 ml of antibiotic solution is pumped to waste. The negative pressure flow of antibiotic solution is then allowed to recirculate through the bone for approximately 15 minutes. Solvent flow is discontinued and the antibiotic solution is decanted and 70% isopropanol is added to the container. Approximately 500 mls of isopropanol is drawn through the bone graft using a negative pressure flow and pumped to waste. The negative pressure solvent flow is then recirculated for approximately 15 minutes. The isopropanol is decanted after solvent flow is stopped and the container is refilled with sterile deionized endotoxin-free water. Approximately 500 mls of water is drawn through the bone graft and directed to waste. The negative pressure flow of water is then recirculated for approximately 15 minutes. Finally, the water is decanted, the bone graft is removed from the container and the solvent line and tapping port removed. Any remaining soft tissue may be removed at this time and the bone graft is now ready for further processing into small bone grafts as required.

EXAMPLE VII

A femur (1) is thawed, and a hole (2) approximately ¼ to ⅝ inch outside diameter is drilled in the bone shaft approximately midway between the distal and proximal ends of the bone. The hole (2) need only be drilled deep enough to penetrate the cortical bone such that the tapping port (3) (FIG. 5) may be securely inserted into the hole. The solvent line (4) is attached securely to the tapping port. Two liters of a solution of 10% ethanol and Allowash™ Solution at a concentration of 0.01X are added to a container designed to hold approximately 3 liters and the bone graft with attached solvent line is placed into the container, immersing it towards the bottom of the container. The temperature of the cleaning solution was adjusted to 45° C. prior to addition of the bone graft and the container with bone graft is placed onto a warming plate, also at 45° C. A negative pressure solvent flow, 1,000 to 1,500 mls/minute, is applied to the system. The flow rate of solution through the bone graft is maintained at approximately 1,200 mls per minute by adjusting the pump rate of the peristaltic pump.

The solution collected in the disposable container is initially dark red(ish), turning to a color similar to that of serum as bone marrow is removed from the graft. By sampling the effluent material being removed from the bone graft it is possible to monitor completion of bone marrow removal by measuring absorbance at 410 nm and it is thus possible to determine when essentially all of the bone marrow is removed from the bone graft. After drawing approximately 3 liters of solution to waste through the bone graft over 15 minutes, the solvent flow is discontinued the container is refilled with 1 to 3 liters of 3% hydrogen peroxide (vol:vol) in endotoxin-free deionized/distilled water and a negative pressure solvent flow is reapplied to the system. The hydrogen peroxide deionized/distilled water solution is drawn through the bone graft at approximately 1100 mls per minute for 15 minutes to remove the detergent solution. Following the removal of detergent solution from the bone graft, solvent flow is discontinued to the system and the bone graft is removed from the container and the solvent line and tapping port removed. The bone graft is now ready for further processing into small bone grafts as required.

EXAMPLE VIII

Figure 9:
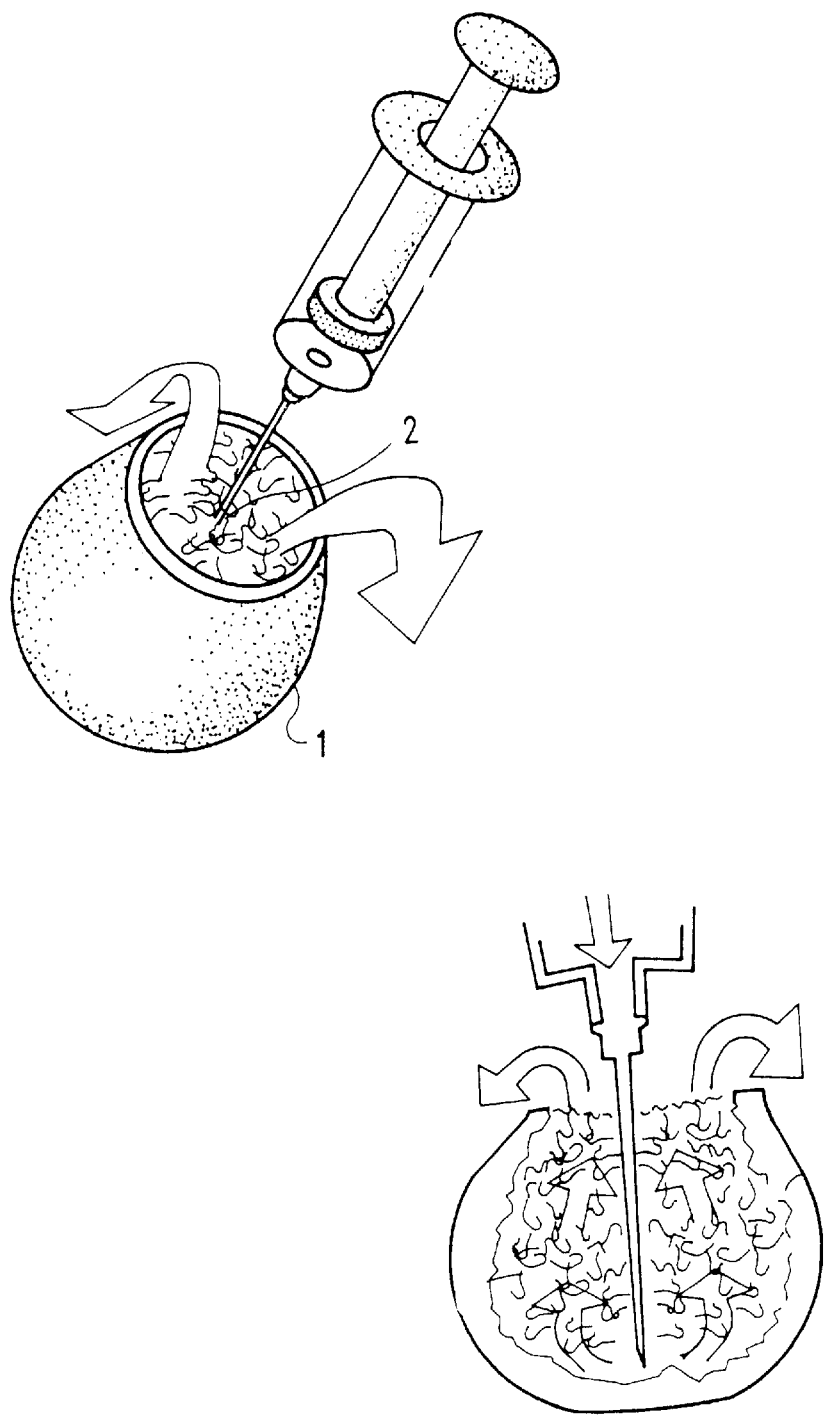
FIG. 9.

For cleaning smaller portions of an essentially intact bone graft, for example femur heads (FIG. 9), it is not necessary to use the plastic containers, or the pressure induced flow of flushing and/or washing solutions. Instead, a large volume syringe with an approximate 18 gauge needle may be used to cause a flow of solutions through the cancellous bone space in the smaller portions of the essentially intact bone grafts. In the cleaning process illustrated in FIG. 9, a femur head is cut from the proximal end of a femur. A small hole (2) is drilled in the approximate center of the cut cross-sectional area to a depth approximating the beginning of the cortical bone distally to the point at which the hole is initiated. The diameter of the hole should be slightly smaller than the outside diameter of the needle which is to be inserted. Once the needle is inserted, flow of cleaning solution may be caused to occur by means of pressure applied on the syringe plunger in the syringe attached to the needle inserted into the cancellous bone space of the small bone graft, for example, the femur head as illustrated in FIG. 9. The cleaning solutions utilized are equivalent to those described in previous examples given. Cleaning solutions may be removed from the cancellous bone space by attaching a fresh syringe to the needle and flushing endotoxin-free ultrapure water through the cancellous bone space. The volumes of cleaning solutions necessary to clean a typical femur head, as illustrated, may range from 200 mls to 500 mls with the preferred volume being 250 to 300 mls. The volumes of washing solutions necessary to remove residual cleaning solution from a typical femur head, as illustrated, may range from 50 mls to 200 mls, with the preferred volume being 100 to 150 mls.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims. All references including patents and co-pending patent applications cited herein are hereby incorporated herein by reference in their entirety.

What is claimed:

1. A method for producing an essentially intact bone graft suitable for transplantation into a human, comprising:
   inducing a negative pressure mediated flow of a first volume of a first solvent, said first solvent comprising one or more detergents, through said essentially intact bone graft, and
   sonicating said essentially intact bone graft in an ultrasonic cleaner, wherein said inducing is carried out simultaneously with said sonicating, wherein said negative pressure mediated flow and said sonicating are carried out for a time effective to produce a cleaned bone graft essentially free from bone marrow.

2. The method of claim 1, wherein a first volume of said first solvent is drawn through said essentially intact bone graft and is collected as waste.

3. The method of claim 2, further comprising:
   inducing a negative pressure mediated flow of a second volume of said first solvent through said essentially intact bone graft, wherein said second volume of said first solvent is recirculated through said essentially intact bone graft.

4. The method of claim 3, further comprising:
   inducing a negative pressure mediated flow of a second solvent, said second solvent comprising a decontaminating agent, through said essentially intact bone graft to produce a decontaminated intact bone graft.

5. The method of claim 4, wherein a first volume of said second solvent is drawn through said essentially intact bone graft and is collected as waste.

6. A method for producing an essentially intact bone graft suitable for transplantation into a human, comprising:
   inducing a negative pressure mediated flow of a first volume of a first solvent, said first solvent comprising one or more detergents, through said essentially intact bone graft;
   inducing a negative pressure mediated flow of a second volume of said first solvent through said essentially intact bone graft wherein said second volume of said first solvent is recirculated through said essentially intact bone graft, and
   inducing a negative pressure mediated flow of a second solvent, said second solvent comprising a decontaminating agent, through said essentially intact bone graft to produce a decontaminated intact bone graft.

7. The method of claim 6, wherein a first volume of said second solvent is drawn through said essentially intact bone graft and is collected as waste.

8. The method of claim 7, further comprising:
   inducing a negative pressure mediated flow of a second volume of said second solvent through said decontaminated intact bone graft, wherein said second volume of said second solvent is recirculated through said essentially intact bone graft.

9. The method of any one of claims 7, 8, 2, or 5, wherein said waste is collected in an essentially closed system.

10. A method for removing bone marrow from an essentially intact bone graft, comprising:
    inducing a pressure mediated flow of solvent through said essentially intact bone graft, wherein said pressure mediated flow is carried out for a time effective to remove said bone marrow from said essentially intact bone graft, and
    sonicating said essentially intact bone graft in an ultrasonic cleaner, wherein said inducing is carried out simultaneously with said sonicating.

11. The method of claim 10, wherein said flow of solvent is mediated at a positive pressure of 1 atmosphere or greater.

12. The method of claim 5, further comprising:
    inducing a negative pressure mediated flow of a second volume of said second solvent through said decontaminated intact bone graft, wherein said second volume of said second solvent is recirculated through said decontaminated intact bone graft.

13. A method for reducing an initial quantity of viral particles and bacterial particles present in an essentially intact bone graft, comprising:
    inducing a pressure mediated flow of solvent through said essentially intact bone graft to produce a cleaned bone graft, and
    sonicating said essentially intact bone graft in an ultrasonic cleaner, wherein said inducing is carried out simultaneously with said sonicating, and wherein a quantity of viral and bacterial particles present in said cleaned bone graft is less than said initial quantity of viral particles and bacterial particles.

14. The method of any one of claims 10, 13, 1, 3, or 12, wherein said ultrasonic cleaner is operated in a range of from 40 KHz to 47 KHz.

15. An essentially intact bone graft suitable for transplantation into a human, produced by the process as claimed in any one of claims 10, 13, 1, 3, or 12.

16. A method for removing bone marrow from an essentially intact bone graft, comprising:
    inducing a negative pressure mediated flow of solvent through said essentially intact bone graft, wherein said negative pressure mediated flow is carried out for a time effective to remove said bone marrow from said essentially intact bone graft.

17. The method of claim 16, wherein said negative pressure mediated flow is induced, and effluent solvent solubilized bone marrow is collected, in an essentially closed system.

18. A method for reducing an initial quantity of viral particles and bacterial particles present in an essentially intact bone graft, comprising:
    inducing a negative pressure mediated flow of solvent through said essentially intact bone graft to produce a cleaned bone graft, wherein a quantity of viral and bacterial particles present in said cleaned bone graft is less than said initial quantity of viral particles and bacterial particles.

19. The method of claim 10, wherein said flow of solvent is mediated at a negative pressure below 1 atmosphere.

20. The method of any one of claims 16, 17 or 18, wherein said solvent comprises one or more members selected from the group consisting of:
 a bacteriocidal agent and a viricidal agent.

21. The method of any one of claims 16, 17 or 18, wherein said method is carried out within an essentially closed system.

22. An essentially intact bone graft free from bone marrow elements and suitable for transplantation into a human, produced by the process as claimed in any one of claims 16, 17, or 18.

23. An essentially intact bone graft essentially free from bone marrow elements and essentially free from viral and bacterial contamination, and suitable for transplantation into a human, produced by the process as claimed in any one of claims 16, 17, or 18.

24. A method for producing an essentially intact bone graft suitable for transplantation into a human, comprising:
 inducing a negative pressure mediated flow of a first volume of a first solvent, said first solvent comprising one or more detergents, through said essentially intact bone graft, and
 inducing a negative pressure mediated flow of a second volume of said first solvent through said essentially intact bone graft wherein said second volume of said first solvent is recirculated through said essentially intact bone graft.

25. An essentially intact bone graft suitable for implantation into a human produced by the process as claimed in claim 13.

26. An essentially intact bone graft suitable for transplantation into a human produced by the process as claimed in any one of claims 24, 6, 7, or 8.

27. A method for producing an essentially intact bone graft suitable for transplantation into a human, comprising:
 inducing a negative pressure mediated flow of a first solvent, said first solvent comprising one or more detergents, through an opening in a bone shaft of said essentially intact bone graft to produce a cleaned intact bone graft; wherein said negative pressure mediated flow is carried out for a time effective to produce a cleaned bone graft essentially free from bone marrow.

28. The method of claim 27, wherein a first volume of said first solvent is drawn through said essentially intact bone graft and is collected as waste.

29. The method of claim 28, further comprising:
 inducing a negative pressure mediated flow of a second volume of said first solvent through said opening wherein said second volume of said first solvent is recirculated through said essentially intact bone graft.

30. The method of any one of claims 28 or 29, further comprising:
 inducing a negative pressure mediated flow of a second solvent, said second solvent comprising a decontaminating agent, through said opening to produce a decontaminated intact bone graft.

31. The method of claim 30, wherein a second volume of said second solvent is drawn through said essentially intact bone graft and is collected as waste.

* * * * *